(12) United States Patent
Medina et al.

(10) Patent No.: US 8,505,821 B2
(45) Date of Patent: Aug. 13, 2013

(54) SYSTEM AND METHOD FOR PROVIDING SENSOR QUALITY ASSURANCE

(75) Inventors: Casey V. Medina, Westminster, CO (US); Charles Haisley, Boulder, CO (US); Michelle L. Hodge, Longmont, CO (US)

(73) Assignee: Covidien LP, Mansfield, MA (US)

( * ) Notice: Subject to any disclaimer, the term of this patent is extended or adjusted under 35 U.S.C. 154(b) by 482 days.

(21) Appl. No.: 12/495,007

(22) Filed: Jun. 30, 2009

(65) Prior Publication Data

US 2010/0327063 A1    Dec. 30, 2010

(51) Int. Cl.
*G06K 19/00*    (2006.01)

(52) U.S. Cl.
USPC ............... 235/454; 235/435; 235/439

(58) Field of Classification Search
USPC ................... 235/375, 435, 487, 494
See application file for complete search history.

(56) References Cited

U.S. PATENT DOCUMENTS

| | | |
|---|---|---|
| 3,721,813 A | 3/1973 | Condon et al. |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |

(Continued)

FOREIGN PATENT DOCUMENTS

| | | |
|---|---|---|
| EP | 0352923 | 1/1990 |
| EP | 793942 A2 | 9/1997 |

(Continued)

*Primary Examiner* — Michael G Lee
*Assistant Examiner* — Matthew Mikels
(74) *Attorney, Agent, or Firm* — Fletcher Yoder

(57) ABSTRACT

The present disclosure is generally directed to maintaining sensor quality standards and/or preventing improper remanufacture of sensors, such as pulse oximetry sensors. Present embodiments may include a sensor that includes an optical machine-readable representation of data included on the sensor and/or packaged therewith, and an information element configured to store data corresponding to the data represented by the optical machine-readable representation.

26 Claims, 5 Drawing Sheets

(56) References Cited

U.S. PATENT DOCUMENTS

| | | |
|---|---|---|
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hansmann et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,035,243 A | 7/1991 | Muz |
| 5,040,539 A | 8/1991 | Schmitt et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,084,327 A | 1/1992 | Stengel |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Friedman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,273,036 A | 12/1993 | Kronberg et al. |
| 5,275,159 A | 1/1994 | Griebel |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Friedman et al. |
| 5,311,865 A | 5/1994 | Mayeux |
| 5,313,940 A | 5/1994 | Fuse et al. |
| 5,323,776 A | 6/1994 | Blakeley et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,344,017 A * | 9/1994 | Wittrock ............... 206/459.1 |
| 5,348,003 A | 9/1994 | Caro |
| 5,348,004 A | 9/1994 | Hollub et al. |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |
| 5,353,799 A | 10/1994 | Chance |
| 5,355,880 A | 10/1994 | Thomas et al. |
| 5,355,882 A | 10/1994 | Ukawa et al. |
| 5,361,758 A | 11/1994 | Hall et al. |
| 5,365,066 A | 11/1994 | Krueger, Jr. et al. |
| 5,368,025 A | 11/1994 | Young et al. |
| 5,368,026 A | 11/1994 | Swedlow et al. |
| 5,368,224 A | 11/1994 | Richardson et al. |
| 5,372,136 A | 12/1994 | Steuer et al. |
| 5,377,675 A | 1/1995 | Ruskewicz et al. |
| 5,385,143 A | 1/1995 | Aoyagi |
| 5,387,122 A | 2/1995 | Goldberger et al. |
| 5,390,670 A | 2/1995 | Centa et al. |
| 5,392,777 A | 2/1995 | Swedlow et al. |
| 5,398,680 A | 3/1995 | Polson et al. |
| 5,402,777 A | 4/1995 | Warring et al. |
| 5,411,023 A | 5/1995 | Morris, Sr. et al. |
| 5,411,024 A | 5/1995 | Thomas et al. |
| 5,413,099 A | 5/1995 | Schmidt et al. |
| 5,413,100 A | 5/1995 | Barthelemy et al. |
| 5,413,101 A | 5/1995 | Sugiura |
| 5,413,102 A | 5/1995 | Schmidt et al. |
| 5,417,207 A | 5/1995 | Young et al. |
| 5,421,329 A | 6/1995 | Casciani et al. |
| 5,425,360 A | 6/1995 | Nelson |
| 5,425,362 A | 6/1995 | Siker et al. |
| 5,427,093 A | 6/1995 | Ogawa et al. |
| 5,429,128 A | 7/1995 | Cadell et al. |
| 5,429,129 A | 7/1995 | Lovejoy et al. |
| 5,431,159 A | 7/1995 | Baker et al. |
| 5,431,170 A | 7/1995 | Mathews |
| 5,437,275 A | 8/1995 | Amundsen et al. |
| 5,438,986 A | 8/1995 | Disch et al. |
| 5,448,991 A | 9/1995 | Polson et al. |
| 5,452,717 A | 9/1995 | Branigan et al. |
| 5,465,714 A | 11/1995 | Scheuing |
| 5,469,845 A | 11/1995 | DeLonzor et al. |
| RE35,122 E | 12/1995 | Corenman et al. |

| Patent | Date | Inventor |
|---|---|---|
| 5,474,065 A | 12/1995 | Meathrel et al. |
| 5,482,034 A | 1/1996 | Lewis et al. |
| 5,482,036 A | 1/1996 | Diab et al. |
| 5,483,646 A | 1/1996 | Uchikoga |
| 5,485,847 A | 1/1996 | Baker, Jr. |
| 5,490,505 A | 2/1996 | Diab et al. |
| 5,490,523 A | 2/1996 | Isaacson et al. |
| 5,491,299 A | 2/1996 | Naylor et al. |
| 5,494,032 A | 2/1996 | Robinson et al. |
| 5,497,771 A | 3/1996 | Rosenheimer |
| 5,499,627 A | 3/1996 | Steuer et al. |
| 5,503,148 A | 4/1996 | Pologe et al. |
| 5,505,199 A | 4/1996 | Kim |
| 5,507,286 A | 4/1996 | Solenberger |
| 5,511,546 A | 4/1996 | Hon |
| 5,517,988 A | 5/1996 | Gerhard |
| 5,520,177 A | 5/1996 | Ogawa et al. |
| 5,521,851 A | 5/1996 | Wei et al. |
| 5,522,388 A | 6/1996 | Ishikawa et al. |
| 5,524,617 A | 6/1996 | Mannheimer |
| 5,529,064 A | 6/1996 | Rall et al. |
| 5,533,507 A | 7/1996 | Potratz |
| 5,551,423 A | 9/1996 | Sugiura |
| 5,551,424 A | 9/1996 | Morrison et al. |
| 5,553,614 A | 9/1996 | Chance |
| 5,553,615 A | 9/1996 | Carim et al. |
| 5,555,882 A | 9/1996 | Richardson et al. |
| 5,558,096 A | 9/1996 | Palatnik |
| 5,560,355 A | 10/1996 | Merchant et al. |
| 5,564,417 A | 10/1996 | Chance |
| 5,575,284 A | 11/1996 | Athan et al. |
| 5,575,285 A | 11/1996 | Takanashi et al. |
| 5,577,500 A | 11/1996 | Potratz |
| 5,582,169 A | 12/1996 | Oda et al. |
| 5,584,296 A | 12/1996 | Cui et al. |
| 5,588,425 A | 12/1996 | Sackner et al. |
| 5,588,427 A | 12/1996 | Tien |
| 5,590,652 A | 1/1997 | Inai |
| 5,595,176 A | 1/1997 | Yamaura |
| 5,596,986 A | 1/1997 | Goldfarb |
| 5,611,337 A | 3/1997 | Bukta |
| 5,617,852 A | 4/1997 | MacGregor |
| 5,619,992 A | 4/1997 | Guthrie et al. |
| 5,626,140 A | 5/1997 | Feldman et al. |
| 5,630,413 A | 5/1997 | Thomas et al. |
| 5,632,272 A | 5/1997 | Diab et al. |
| 5,632,273 A | 5/1997 | Suzuki |
| 5,634,459 A | 6/1997 | Gardosi |
| 5,638,593 A | 6/1997 | Gerhardt et al. |
| 5,638,818 A | 6/1997 | Diab et al. |
| 5,645,060 A | 7/1997 | Yorkey et al. |
| 5,645,440 A | 7/1997 | Tobler et al. |
| 5,660,567 A | 8/1997 | Nierlich et al. |
| 5,662,105 A | 9/1997 | Tien |
| 5,662,106 A | 9/1997 | Swedlow et al. |
| 5,666,952 A | 9/1997 | Fuse et al. |
| 5,671,529 A | 9/1997 | Nelson |
| 5,673,692 A | 10/1997 | Schulze et al. |
| 5,673,693 A | 10/1997 | Solenberger |
| 5,676,139 A | 10/1997 | Goldberger et al. |
| 5,676,141 A | 10/1997 | Hollub |
| 5,678,544 A | 10/1997 | DeLonzor et al. |
| 5,680,857 A | 10/1997 | Pelikan et al. |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,692,503 A | 12/1997 | Kuenstner |
| 5,692,505 A | 12/1997 | Fouts |
| 5,709,205 A | 1/1998 | Bukta |
| 5,713,355 A | 2/1998 | Richardson et al. |
| 5,724,967 A | 3/1998 | Venkatachalam |
| 5,727,547 A | 3/1998 | Levinson et al. |
| 5,731,582 A | 3/1998 | West |
| D393,830 S | 4/1998 | Tobler et al. |
| 5,743,260 A | 4/1998 | Chung et al. |
| 5,743,263 A | 4/1998 | Baker, Jr. |
| 5,746,206 A | 5/1998 | Mannheimer |
| 5,746,697 A | 5/1998 | Swedlow et al. |
| 5,752,914 A | 5/1998 | DeLonzor et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,766,125 A | 6/1998 | Aoyagi et al. |
| 5,766,127 A | 6/1998 | Pologe et al. |
| 5,769,785 A | 6/1998 | Diab et al. |
| 5,772,587 A | 6/1998 | Gratton et al. |
| 5,774,213 A | 6/1998 | Trebino et al. |
| 5,776,058 A | 7/1998 | Levinson et al. |
| 5,776,059 A | 7/1998 | Kaestle |
| 5,779,630 A | 7/1998 | Fein et al. |
| 5,779,631 A | 7/1998 | Chance |
| 5,782,237 A | 7/1998 | Casciani et al. |
| 5,782,756 A | 7/1998 | Mannheimer |
| 5,782,757 A | 7/1998 | Diab et al. |
| 5,782,758 A | 7/1998 | Ausec et al. |
| 5,786,592 A | 7/1998 | Hök |
| 5,790,729 A | 8/1998 | Pologe et al. |
| 5,792,052 A | 8/1998 | Isaacson et al. |
| 5,795,292 A | 8/1998 | Lewis et al. |
| 5,797,841 A | 8/1998 | DeLonzor et al. |
| 5,800,348 A | 9/1998 | Kaestle |
| 5,800,349 A | 9/1998 | Isaacson et al. |
| 5,803,910 A | 9/1998 | Potratz |
| 5,807,246 A | 9/1998 | Sakaguchi et al. |
| 5,807,247 A | 9/1998 | Merchant et al. |
| 5,807,248 A | 9/1998 | Mills |
| 5,810,723 A | 9/1998 | Aldrich |
| 5,810,724 A | 9/1998 | Gronvall |
| 5,813,980 A | 9/1998 | Levinson et al. |
| 5,817,008 A | 10/1998 | Rafert et al. |
| 5,817,009 A | 10/1998 | Rosenheimer et al. |
| 5,817,010 A | 10/1998 | Hibl |
| 5,818,985 A | 10/1998 | Merchant et al. |
| 5,820,550 A | 10/1998 | Polson et al. |
| 5,823,950 A | 10/1998 | Diab et al. |
| 5,823,952 A | 10/1998 | Levinson et al. |
| 5,827,182 A | 10/1998 | Raley et al. |
| 5,830,135 A | 11/1998 | Bosque et al. |
| 5,830,136 A | 11/1998 | DeLonzor et al. |
| 5,830,137 A | 11/1998 | Scharf |
| 5,839,439 A | 11/1998 | Nierlich et al. |
| RE36,000 E | 12/1998 | Swedlow et al. |
| 5,842,979 A | 12/1998 | Jarman et al. |
| 5,842,981 A | 12/1998 | Larsen et al. |
| 5,842,982 A | 12/1998 | Mannheimer |
| 5,846,190 A | 12/1998 | Woehrle |
| 5,851,178 A | 12/1998 | Aronow |
| 5,851,179 A | 12/1998 | Ritson et al. |
| 5,853,364 A | 12/1998 | Baker, Jr. et al. |
| 5,860,919 A | 1/1999 | Kiani-Azarbayjany et al. |
| 5,865,736 A | 2/1999 | Baker, Jr. et al. |
| 5,871,442 A | 2/1999 | Madarasz et al. |
| 5,879,294 A | 3/1999 | Anderson et al. |
| 5,885,213 A | 3/1999 | Richardson et al. |
| 5,890,929 A | 4/1999 | Mills et al. |
| 5,891,021 A | 4/1999 | Dillon et al. |
| 5,891,022 A | 4/1999 | Pologe |
| 5,891,024 A | 4/1999 | Jarman et al. |
| 5,891,025 A | 4/1999 | Buschmann et al. |
| 5,891,026 A | 4/1999 | Wang et al. |
| 5,902,235 A | 5/1999 | Lewis et al. |
| 5,910,108 A | 6/1999 | Solenberger |
| 5,911,690 A | 6/1999 | Rall |
| 5,912,656 A | 6/1999 | Tham et al. |
| 5,913,819 A | 6/1999 | Taylor et al. |
| 5,916,154 A | 6/1999 | Hobbs et al. |
| 5,916,155 A | 6/1999 | Levinson et al. |
| 5,919,133 A | 7/1999 | Taylor et al. |
| 5,919,134 A | 7/1999 | Diab |
| 5,920,263 A | 7/1999 | Huttenhoff et al. |
| 5,921,921 A | 7/1999 | Potratz et al. |
| 5,922,607 A | 7/1999 | Bernreuter |
| 5,924,979 A | 7/1999 | Swedlow et al. |
| 5,924,980 A | 7/1999 | Coetzee |
| 5,924,982 A | 7/1999 | Chin |
| 5,924,985 A | 7/1999 | Jones |
| 5,934,277 A | 8/1999 | Mortz |

| Patent | Date | Inventor |
|---|---|---|
| 5,934,925 A | 8/1999 | Tobler et al. |
| 5,940,182 A | 8/1999 | Lepper, Jr. et al. |
| 5,954,644 A | 9/1999 | Dettling et al. |
| 5,960,610 A | 10/1999 | Levinson et al. |
| 5,961,450 A | 10/1999 | Merchant et al. |
| 5,961,452 A | 10/1999 | Chung et al. |
| 5,964,701 A | 10/1999 | Asada et al. |
| 5,971,930 A | 10/1999 | Elghazzawi |
| 5,978,691 A | 11/1999 | Mills |
| 5,978,693 A | 11/1999 | Hamilton et al. |
| 5,983,122 A | 11/1999 | Jarman et al. |
| 5,987,343 A | 11/1999 | Kinast |
| 5,991,648 A | 11/1999 | Levin |
| 5,995,855 A | 11/1999 | Kiani et al. |
| 5,995,856 A | 11/1999 | Mannheimer et al. |
| 5,995,858 A | 11/1999 | Kinast |
| 5,995,859 A | 11/1999 | Takahashi |
| 5,997,343 A | 12/1999 | Mills et al. |
| 5,999,834 A | 12/1999 | Wang et al. |
| 6,002,952 A | 12/1999 | Diab et al. |
| 6,005,658 A | 12/1999 | Kaluza et al. |
| 6,006,120 A | 12/1999 | Levin |
| 6,011,985 A | 1/2000 | Athan et al. |
| 6,011,986 A | 1/2000 | Diab et al. |
| 6,014,576 A | 1/2000 | Raley |
| 6,018,673 A | 1/2000 | Chin et al. |
| 6,018,674 A | 1/2000 | Aronow |
| 6,022,321 A | 2/2000 | Amano et al. |
| 6,023,541 A | 2/2000 | Merchant et al. |
| 6,026,312 A | 2/2000 | Shemwell et al. |
| 6,026,314 A | 2/2000 | Amerov et al. |
| 6,031,603 A | 2/2000 | Fine et al. |
| 6,035,223 A | 3/2000 | Baker, Jr. |
| 6,036,642 A | 3/2000 | Diab et al. |
| 6,041,247 A | 3/2000 | Weckstrom et al. |
| 6,044,283 A | 3/2000 | Fein et al. |
| 6,047,201 A | 4/2000 | Jackson, III |
| 6,061,584 A | 5/2000 | Lovejoy et al. |
| 6,064,898 A | 5/2000 | Aldrich |
| 6,064,899 A | 5/2000 | Fein et al. |
| 6,067,462 A | 5/2000 | Diab et al. |
| 6,073,038 A | 6/2000 | Wang et al. |
| 6,076,859 A * | 6/2000 | Hall et al. ............. 283/89 |
| 6,078,833 A | 6/2000 | Hueber |
| 6,081,735 A | 6/2000 | Diab et al. |
| 6,081,742 A | 6/2000 | Amano et al. |
| 6,083,157 A | 7/2000 | Noller |
| 6,083,172 A | 7/2000 | Baker, Jr. et al. |
| 6,088,607 A | 7/2000 | Diab et al. |
| 6,094,592 A | 7/2000 | Yorkey et al. |
| 6,095,974 A | 8/2000 | Shemwell et al. |
| 6,104,938 A | 8/2000 | Huiku et al. |
| 6,112,107 A | 8/2000 | Hannula |
| 6,113,541 A | 9/2000 | Dias et al. |
| 6,115,621 A | 9/2000 | Chin |
| 6,122,535 A | 9/2000 | Kaestle et al. |
| 6,133,994 A | 10/2000 | Mathews et al. |
| 6,135,952 A | 10/2000 | Coetzee |
| 6,144,444 A | 11/2000 | Haworth et al. |
| 6,144,867 A | 11/2000 | Walker et al. |
| 6,144,868 A | 11/2000 | Parker |
| 6,149,481 A | 11/2000 | Wang et al. |
| 6,150,951 A | 11/2000 | Olejniczak |
| 6,151,107 A | 11/2000 | Schöllermann et al. |
| 6,151,518 A | 11/2000 | Hayashi |
| 6,152,754 A | 11/2000 | Gerhardt et al. |
| 6,154,667 A | 11/2000 | Miura et al. |
| 6,157,850 A | 12/2000 | Diab et al. |
| 6,163,715 A | 12/2000 | Larsen et al. |
| 6,165,005 A | 12/2000 | Mills et al. |
| 6,173,196 B1 | 1/2001 | Delonzor et al. |
| 6,178,343 B1 | 1/2001 | Bindszus et al. |
| 6,181,958 B1 | 1/2001 | Steuer et al. |
| 6,181,959 B1 | 1/2001 | Schöllermann et al. |
| 6,184,521 B1 | 2/2001 | Coffin, IV et al. |
| 6,188,470 B1 | 2/2001 | Grace |
| 6,192,260 B1 | 2/2001 | Chance |
| 6,195,575 B1 | 2/2001 | Levinson |
| 6,198,951 B1 | 3/2001 | Kosuda et al. |
| 6,206,830 B1 | 3/2001 | Diab et al. |
| 6,213,952 B1 | 4/2001 | Finarov et al. |
| 6,217,523 B1 | 4/2001 | Amano et al. |
| 6,222,189 B1 | 4/2001 | Misner et al. |
| 6,226,539 B1 | 5/2001 | Potratz |
| 6,226,540 B1 | 5/2001 | Bernreuter et al. |
| 6,229,856 B1 | 5/2001 | Diab et al. |
| 6,230,035 B1 | 5/2001 | Aoyagi et al. |
| 6,233,470 B1 | 5/2001 | Tsuchiya |
| 6,236,871 B1 | 5/2001 | Tsuchiya |
| 6,236,872 B1 | 5/2001 | Diab et al. |
| 6,240,305 B1 | 5/2001 | Tsuchiya |
| 6,253,097 B1 | 6/2001 | Aronow et al. |
| 6,253,098 B1 | 6/2001 | Walker et al. |
| 6,256,523 B1 | 7/2001 | Diab et al. |
| 6,256,524 B1 | 7/2001 | Walker et al. |
| 6,261,236 B1 | 7/2001 | Grimblatov |
| 6,263,221 B1 | 7/2001 | Chance et al. |
| 6,263,222 B1 | 7/2001 | Diab et al. |
| 6,263,223 B1 | 7/2001 | Sheperd et al. |
| 6,266,546 B1 | 7/2001 | Steuer et al. |
| 6,266,547 B1 | 7/2001 | Walker et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,894 B1 | 9/2001 | Oppelt et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,308,089 B1 | 10/2001 | Von der Ruhr et al. |
| 6,321,100 B1 | 11/2001 | Parker |
| 6,330,468 B1 | 12/2001 | Scharf |
| 6,334,065 B1 | 12/2001 | Al-Ali et al. |
| 6,339,715 B1 | 1/2002 | Bahr et al. |
| 6,343,223 B1 | 1/2002 | Chin et al. |
| 6,343,224 B1 | 1/2002 | Parker |
| 6,346,886 B1 * | 2/2002 | De La Huerga ............. 340/573.1 |
| 6,349,228 B1 | 2/2002 | Kiani et al. |
| 6,351,658 B1 | 2/2002 | Middleman et al. |
| 6,353,750 B1 | 3/2002 | Kimura et al. |
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| 6,370,408 B1 | 4/2002 | Merchant et al. |
| 6,370,409 B1 | 4/2002 | Chung et al. |
| 6,374,129 B1 | 4/2002 | Chin et al. |
| 6,377,829 B1 | 4/2002 | Al-Ali et al. |
| 6,381,479 B1 | 4/2002 | Norris |
| 6,381,480 B1 | 4/2002 | Stoddar et al. |
| 6,385,471 B1 | 5/2002 | Mortz |
| 6,385,821 B1 | 5/2002 | Modgil et al. |
| 6,388,240 B2 | 5/2002 | Schulz et al. |
| 6,393,310 B1 | 5/2002 | Kuenstner |
| 6,397,091 B2 | 5/2002 | Diab et al. |
| 6,397,092 B1 | 5/2002 | Norris et al. |
| 6,397,093 B1 | 5/2002 | Aldrich |
| 6,400,971 B1 | 6/2002 | Finarov et al. |
| 6,400,972 B1 | 6/2002 | Fine |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,419,671 B1 | 7/2002 | Lemberg |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |

| Patent | Date | Inventor |
|---|---|---|
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,490,466 B1 | 12/2002 | Fein et al. |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B2 | 4/2003 | Gurley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,510 B2 | 8/2003 | Swedlow et al. |
| 6,606,511 B1 | 8/2003 | Ali et al. |
| 6,606,512 B2 | 8/2003 | Muz et al. |
| 6,615,064 B1 | 9/2003 | Aldrich |
| 6,615,065 B1 | 9/2003 | Barrett et al. |
| 6,618,602 B2 | 9/2003 | Levin |
| 6,622,034 B1 | 9/2003 | Gorski et al. |
| 6,628,975 B1 | 9/2003 | Fein et al. |
| 6,631,281 B1 | 10/2003 | Kästle |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Pishney et al. |
| 6,658,277 B2 | 12/2003 | Wassermann |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neill et al. |
| 6,754,515 B1 | 6/2004 | Pologe |
| 6,754,516 B2 | 6/2004 | Mannheimer |
| 6,760,607 B2 | 7/2004 | Al-All |
| 6,760,609 B2 | 7/2004 | Jacques |
| 6,760,610 B2 | 7/2004 | Tschupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckström |
| 6,792,300 B1 | 9/2004 | Diab et al. |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |

| | | |
|---|---|---|
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,879,850 B2 | 4/2005 | Kimball |
| 6,882,874 B2 | 4/2005 | Huiku |
| 6,889,153 B2 | 5/2005 | Dietiker |
| 6,898,452 B2 | 5/2005 | Al-Ali et al. |
| 6,909,912 B2 | 6/2005 | Melker |
| 6,912,413 B2 | 6/2005 | Rantala et al. |
| 6,916,289 B2 | 7/2005 | Schnall |
| 6,920,345 B2 | 7/2005 | Al-Ali et al. |
| 6,931,269 B2 | 8/2005 | Terry |
| 6,934,570 B2 | 8/2005 | Kiani et al. |
| 6,939,307 B1 | 9/2005 | Dunlop |
| 6,941,162 B2 | 9/2005 | Fudge et al. |
| 6,947,781 B2 | 9/2005 | Asada et al. |
| 6,950,687 B2 | 9/2005 | Al-Ali |
| 6,963,767 B2 | 11/2005 | Rantala et al. |
| 6,971,580 B2 | 12/2005 | DeLonzor et al. |
| 6,979,812 B2 | 12/2005 | Al-Ali |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Al-Ali |
| 6,992,772 B2 | 1/2006 | Block et al. |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali et al. |
| 7,027,850 B2 | 4/2006 | Wasserman |
| 7,035,697 B1 | 4/2006 | Brown |
| 7,039,449 B2 | 5/2006 | Al-Ali |
| 7,043,289 B2 | 5/2006 | Fine et al. |
| 7,047,055 B2 | 5/2006 | Boaz et al. |
| 7,047,056 B2 | 5/2006 | Hannula et al. |
| 7,048,687 B1 | 5/2006 | Reuss et al. |
| 7,060,035 B2 | 6/2006 | Wasserman et al. |
| 7,062,307 B2 | 6/2006 | Norris et al. |
| 7,067,893 B2 | 6/2006 | Mills et al. |
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |
| 7,096,052 B2 | 8/2006 | Mason et al. |
| 7,096,054 B2 | 8/2006 | Abdul-Hafiz et al. |
| 7,107,088 B2 | 9/2006 | Aceti |
| 7,113,815 B2 | 9/2006 | O'Neil et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,139,599 B2 | 11/2006 | Terry |
| 7,142,901 B2 | 11/2006 | Kiani et al. |
| 7,162,288 B2 | 1/2007 | Nordstrom |
| 7,181,264 B2 | 2/2007 | Wiesmann et al. |
| 7,186,966 B2 | 3/2007 | Al-Ali |
| 7,190,987 B2 | 3/2007 | Lindekugel et al. |
| 7,198,778 B2 | 4/2007 | Mannheimer et al. |
| 7,209,775 B2 | 4/2007 | Bae et al. |
| 7,215,984 B2 | 5/2007 | Diab et al. |
| 7,225,006 B2 | 5/2007 | Al-Ali et al. |
| 7,236,811 B2 | 6/2007 | Schmitt |
| 7,248,910 B2 | 7/2007 | Li et al. |
| 7,254,433 B2 | 8/2007 | Diab et al. |
| 7,254,434 B2 | 8/2007 | Schulz et al. |
| 7,263,395 B2 | 8/2007 | Chan et al. |
| 7,272,425 B2 | 9/2007 | Al-Ali |
| 7,272,426 B2 | 9/2007 | Scmid |
| 7,280,858 B2 | 10/2007 | Al-Ali et al. |
| 7,295,866 B2 | 11/2007 | Al-Ali et al. |
| 7,305,262 B2 | 12/2007 | Brodnick et al. |
| 7,315,753 B2 | 1/2008 | Baker, Jr. et al. |
| 7,375,347 B2 | 5/2008 | Colvin, Jr. et al. |
| 7,423,526 B2 | 9/2008 | Despotis |
| 7,430,444 B2 | 9/2008 | Pologe et al. |
| 7,438,687 B2 | 10/2008 | Lewicke |
| 7,457,652 B2 | 11/2008 | Porges et al. |
| 2001/0021803 A1 | 9/2001 | Blank et al. |
| 2001/0051767 A1 | 12/2001 | Williams et al. |
| 2002/0026109 A1 | 2/2002 | Diab et al. |
| 2002/0028990 A1 | 3/2002 | Shepherd et al. |
| 2002/0038078 A1 | 3/2002 | Ito |
| 2002/0042558 A1 | 4/2002 | Mendelson |
| 2002/0056756 A1* | 5/2002 | Cameron et al. ............... 235/468 |
| 2002/0068859 A1 | 6/2002 | Knopp |
| 2002/0128544 A1 | 9/2002 | Diab et al. |
| 2002/0133067 A1 | 9/2002 | Jackson, III |
| 2002/0156354 A1 | 10/2002 | Larson |
| 2002/0173706 A1 | 11/2002 | Takatani |
| 2002/0173709 A1 | 11/2002 | Fine et al. |
| 2002/0190863 A1 | 12/2002 | Lynn |
| 2002/0198442 A1 | 12/2002 | Rantala et al. |
| 2003/0018243 A1 | 1/2003 | Gerhardt et al. |
| 2003/0036690 A1 | 2/2003 | Geddes et al. |
| 2003/0045785 A1 | 3/2003 | Diab et al. |
| 2003/0073889 A1 | 4/2003 | Keilbach et al. |
| 2003/0073890 A1 | 4/2003 | Hanna |
| 2003/0100840 A1 | 5/2003 | Sugiura et al. |
| 2003/0132495 A1 | 7/2003 | Mills et al. |
| 2003/0135099 A1 | 7/2003 | Al-Ali |
| 2003/0162414 A1 | 8/2003 | Schulz et al. |
| 2003/0171662 A1 | 9/2003 | O'Connor et al. |
| 2003/0176776 A1 | 9/2003 | Huiku |
| 2003/0181799 A1 | 9/2003 | Lindekugel et al. |
| 2003/0187337 A1 | 10/2003 | Tarassenko et al. |
| 2003/0195402 A1 | 10/2003 | Fein et al. |
| 2003/0197679 A1 | 10/2003 | Ali et al. |
| 2003/0212316 A1 | 11/2003 | Leiden et al. |
| 2003/0225323 A1 | 12/2003 | Kiani et al. |
| 2003/0225337 A1 | 12/2003 | Scharf et al. |
| 2003/0236452 A1 | 12/2003 | Melker et al. |
| 2003/0236647 A1 | 12/2003 | Yoon et al. |
| 2004/0006261 A1 | 1/2004 | Swedlow et al. |
| 2004/0010188 A1 | 1/2004 | Wasserman et al. |
| 2004/0024297 A1 | 2/2004 | Chen et al. |
| 2004/0024326 A1 | 2/2004 | Yeo et al. |
| 2004/0034293 A1 | 2/2004 | Kimball |
| 2004/0039272 A1 | 2/2004 | Abdul-Hafiz et al. |
| 2004/0039273 A1 | 2/2004 | Terry |
| 2004/0054269 A1 | 3/2004 | Rantala et al. |
| 2004/0054291 A1 | 3/2004 | Schulz et al. |
| 2004/0059209 A1 | 3/2004 | Al-Ali et al. |
| 2004/0059210 A1 | 3/2004 | Stetson |
| 2004/0064020 A1 | 4/2004 | Diab et al. |
| 2004/0068164 A1 | 4/2004 | Diab et al. |
| 2004/0087846 A1 | 5/2004 | Wasserman |
| 2004/0092805 A1 | 5/2004 | Yarita |
| 2004/0098009 A1 | 5/2004 | Boecker et al. |
| 2004/0107065 A1 | 6/2004 | Al-Ali et al. |
| 2004/0116788 A1 | 6/2004 | Chernoguz et al. |
| 2004/0116789 A1 | 6/2004 | Boaz et al. |
| 2004/0117891 A1 | 6/2004 | Hannula et al. |
| 2004/0122300 A1 | 6/2004 | Boas et al. |
| 2004/0122302 A1 | 6/2004 | Mason et al. |
| 2004/0133087 A1 | 7/2004 | Ali et al. |
| 2004/0133088 A1 | 7/2004 | Al-Ali et al. |
| 2004/0138538 A1 | 7/2004 | Stetson |
| 2004/0138540 A1 | 7/2004 | Baker, Jr. et al. |
| 2004/0143172 A1 | 7/2004 | Fudge et al. |
| 2004/0147821 A1 | 7/2004 | Al-Ali et al. |
| 2004/0147822 A1 | 7/2004 | Al-Ali et al. |
| 2004/0147823 A1 | 7/2004 | Kiani et al. |
| 2004/0147824 A1 | 7/2004 | Diab et al. |
| 2004/0152965 A1 | 8/2004 | Diab et al. |
| 2004/0158134 A1 | 8/2004 | Diab et al. |
| 2004/0158135 A1 | 8/2004 | Baker, Jr. et al. |

| | | |
|---|---|---|
| 2004/0162472 A1 | 8/2004 | Berson et al. |
| 2004/0171920 A1 | 9/2004 | Mannheimer et al. |
| 2004/0171948 A1 | 9/2004 | Terry |
| 2004/0176671 A1 | 9/2004 | Fine et al. |
| 2004/0177032 A1* | 9/2004 | Bradley et al. .................. 705/38 |
| 2004/0181133 A1 | 9/2004 | Al-Ali et al. |
| 2004/0181134 A1 | 9/2004 | Baker, Jr. et al. |
| 2004/0186358 A1 | 9/2004 | Chernow et al. |
| 2004/0199063 A1 | 10/2004 | O'Neil et al. |
| 2004/0204636 A1 | 10/2004 | Diab et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215069 A1 | 10/2004 | Mannheimer |
| 2004/0230107 A1 | 11/2004 | Asada et al. |
| 2004/0230108 A1 | 11/2004 | Melker et al. |
| 2004/0236196 A1 | 11/2004 | Diab et al. |
| 2004/0242980 A1 | 12/2004 | Kiani et al. |
| 2004/0249252 A1 | 12/2004 | Fine et al. |
| 2004/0257557 A1 | 12/2004 | Block et al. |
| 2004/0260161 A1 | 12/2004 | Melker et al. |
| 2004/0267103 A1 | 12/2004 | Li et al. |
| 2004/0267104 A1 | 12/2004 | Hannula et al. |
| 2004/0267140 A1 | 12/2004 | Ito et al. |
| 2005/0004479 A1 | 1/2005 | Townsend et al. |
| 2005/0010092 A1 | 1/2005 | Weber et al. |
| 2005/0020887 A1 | 1/2005 | Goldberg |
| 2005/0020894 A1 | 1/2005 | Norris et al. |
| 2005/0033128 A1 | 2/2005 | Ali et al. |
| 2005/0033129 A1 | 2/2005 | Edgar, Jr. et al. |
| 2005/0043599 A1 | 2/2005 | O'Mara |
| 2005/0043600 A1 | 2/2005 | Diab et al. |
| 2005/0049470 A1 | 3/2005 | Terry |
| 2005/0049471 A1 | 3/2005 | Aceti |
| 2005/0075550 A1 | 4/2005 | Lindekugel |
| 2005/0113651 A1 | 5/2005 | Wood et al. |
| 2005/0177034 A1 | 8/2005 | Beaumont |
| 2005/0192845 A1* | 9/2005 | Brinsfield et al. .................. 705/3 |
| 2005/0197548 A1 | 9/2005 | Dietiker |
| 2005/0228248 A1 | 10/2005 | Dietiker |
| 2005/0277819 A1 | 12/2005 | Kiani et al. |
| 2005/0283059 A1 | 12/2005 | Iyer et al. |
| 2006/0025660 A1 | 2/2006 | Swedlow et al. |
| 2006/0030762 A1 | 2/2006 | David et al. |
| 2006/0030764 A1 | 2/2006 | Porges et al. |
| 2006/0030765 A1 | 2/2006 | Swedlow et al. |
| 2006/0032917 A1* | 2/2006 | Ritter ........................ 235/385 |
| 2006/0058594 A1 | 3/2006 | Ishizuka et al. |
| 2006/0084852 A1 | 4/2006 | Mason et al. |
| 2006/0089547 A1 | 4/2006 | Sarussi |
| 2006/0106294 A1 | 5/2006 | Maser et al. |
| 2006/0109105 A1* | 5/2006 | Varner et al. ............. 340/539.12 |
| 2006/0161054 A1 | 7/2006 | Reuss et al. |
| 2006/0195028 A1 | 8/2006 | Hannula et al. |
| 2006/0206020 A1 | 9/2006 | Liao et al. |
| 2006/0217604 A1 | 9/2006 | Fein et al. |
| 2006/0217605 A1 | 9/2006 | Fein et al. |
| 2006/0217606 A1 | 9/2006 | Fein et al. |
| 2006/0217607 A1 | 9/2006 | Fein et al. |
| 2006/0217608 A1 | 9/2006 | Fein et al. |
| 2006/0224058 A1 | 10/2006 | Mannheimer |
| 2006/0224059 A1 | 10/2006 | Swedlow et al. |
| 2006/0229510 A1 | 10/2006 | Fein et al. |
| 2006/0229511 A1 | 10/2006 | Fein et al. |
| 2006/0247501 A1 | 11/2006 | Ali |
| 2006/0258921 A1 | 11/2006 | Addison et al. |
| 2006/0276700 A1 | 12/2006 | O'Neil et al. |
| 2007/0032710 A1 | 2/2007 | Raridan et al. |
| 2007/0032712 A1 | 2/2007 | Raridan et al. |
| 2007/0032715 A1 | 2/2007 | Eghbal et al. |
| 2007/0043269 A1 | 2/2007 | Mannheimer et al. |
| 2007/0043270 A1 | 2/2007 | Mannheimer et al. |
| 2007/0043271 A1 | 2/2007 | Mannheimer et al. |
| 2007/0043272 A1 | 2/2007 | Mannheimer et al. |
| 2007/0043273 A1 | 2/2007 | Mannheimer et al. |
| 2007/0043274 A1 | 2/2007 | Mannheimer et al. |
| 2007/0043275 A1 | 2/2007 | Manheimer et al. |
| 2007/0043276 A1 | 2/2007 | Mannheimer et al. |
| 2007/0043277 A1 | 2/2007 | Mannheimer et al. |
| 2007/0043278 A1 | 2/2007 | Mannheimer et al. |
| 2007/0043279 A1 | 2/2007 | Mannheimer et al. |
| 2007/0043280 A1 | 2/2007 | Mannheimer et al. |
| 2007/0043282 A1 | 2/2007 | Mannheimer et al. |
| 2007/0049810 A1 | 3/2007 | Mannheimer et al. |
| 2007/0073116 A1 | 3/2007 | Kiani et al. |
| 2007/0073121 A1 | 3/2007 | Hoarau et al. |
| 2007/0073125 A1 | 3/2007 | Hoarau et al. |
| 2007/0073126 A1 | 3/2007 | Raridan, Jr. |
| 2007/0073128 A1 | 3/2007 | Hoarau et al. |
| 2007/0088207 A1 | 4/2007 | Mannheimer et al. |
| 2007/0129622 A1 | 6/2007 | Bourget et al. |
| 2007/0156034 A1 | 7/2007 | Al-Ali |
| 2007/0244825 A1* | 10/2007 | Semmer et al. .................. 705/59 |
| 2008/0014117 A1* | 1/2008 | Questel et al. .................. 422/56 |
| 2008/0030346 A1* | 2/2008 | Despotis .................... 340/572.9 |
| 2008/0081967 A1 | 4/2008 | Andersohn et al. |
| 2008/0081971 A1 | 4/2008 | Ollerdessen |
| 2008/0088467 A1 | 4/2008 | Al-Ali |
| 2008/0091089 A1 | 4/2008 | Guillory et al. |
| 2008/0091090 A1 | 4/2008 | Guillory et al. |
| 2008/0144053 A1* | 6/2008 | Gudan et al. .................... 358/1.8 |
| 2008/0221410 A1 | 9/2008 | Campbell et al. |
| 2008/0221414 A1 | 9/2008 | Baker, Jr. |
| 2008/0287757 A1 | 11/2008 | Berson et al. |

FOREIGN PATENT DOCUMENTS

| | | |
|---|---|---|
| JP | 24113353 A | 4/2004 |
| JP | 27020836 A2 | 2/2007 |
| JP | 27330708 A2 | 12/2007 |
| WO | WO9316629 | 9/1993 |
| WO | WO03011127 | 2/2003 |
| WO | 2006005169 A1 | 1/2006 |
| WO | 2006109072 A2 | 10/2006 |

* cited by examiner

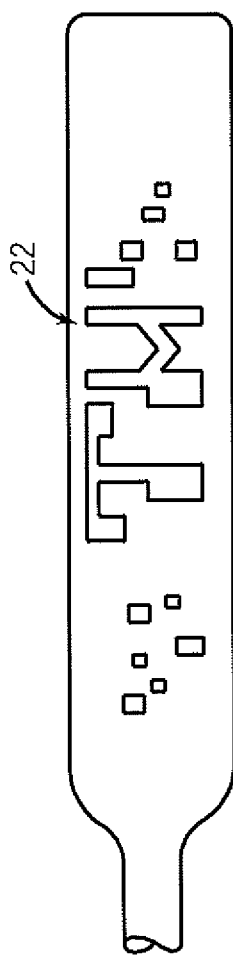
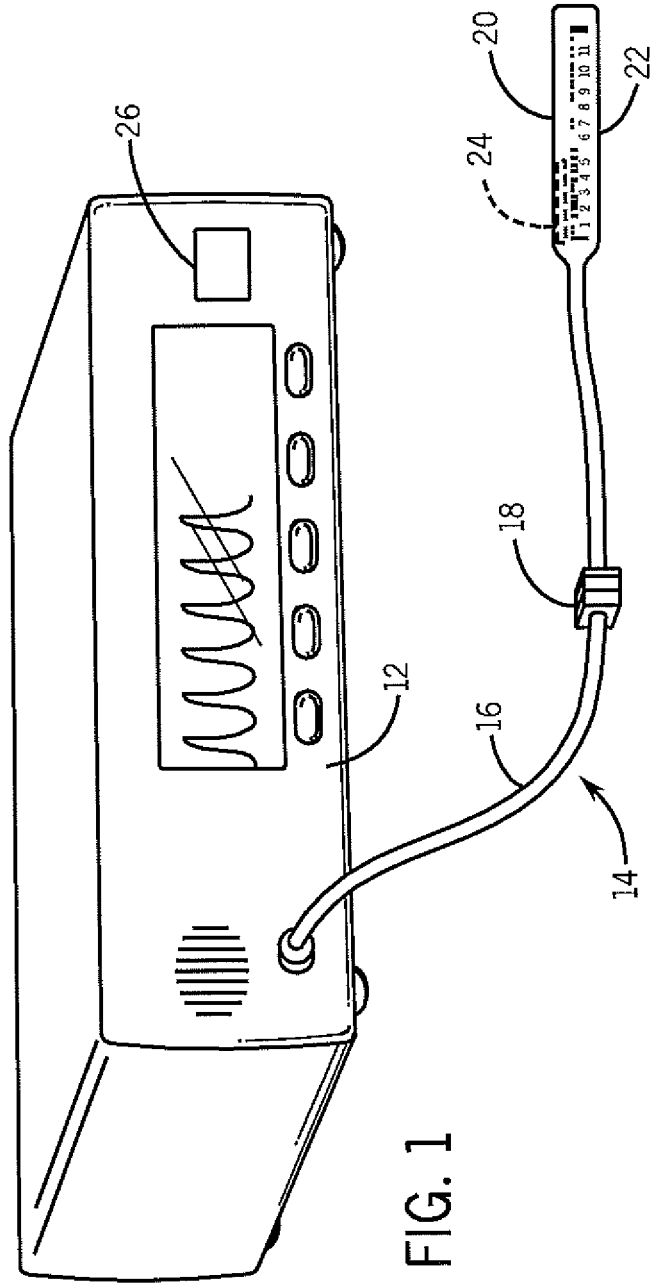
FIG. 2
FIG. 1

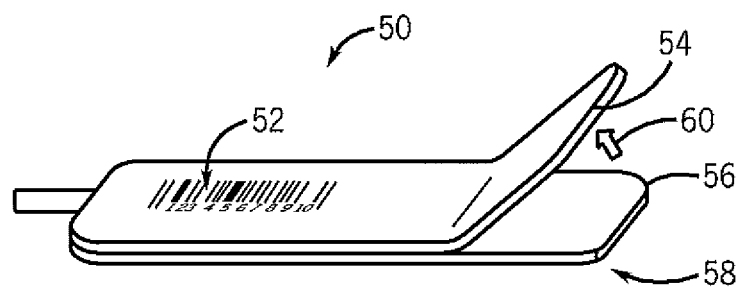
FIG. 7
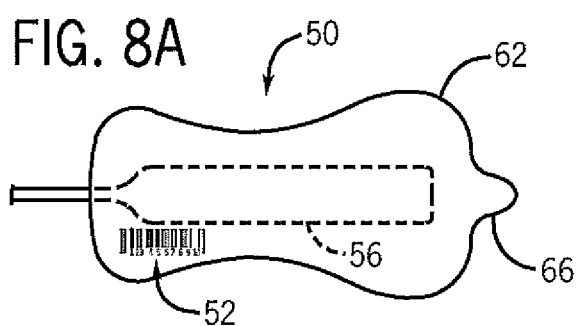
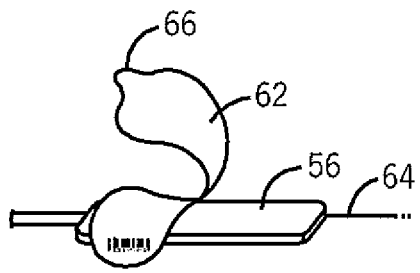
FIG. 8A
FIG. 8B
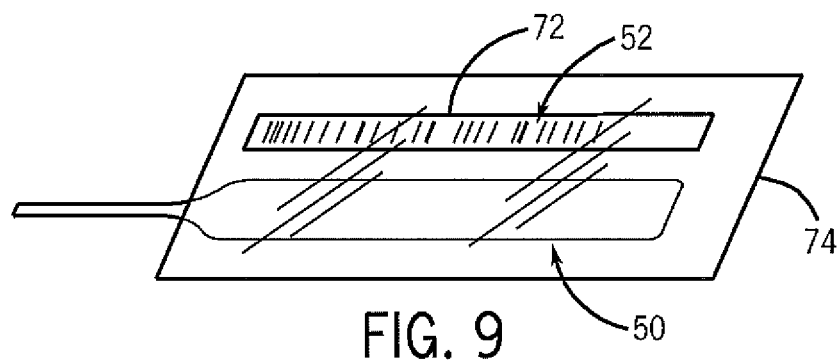
FIG. 9

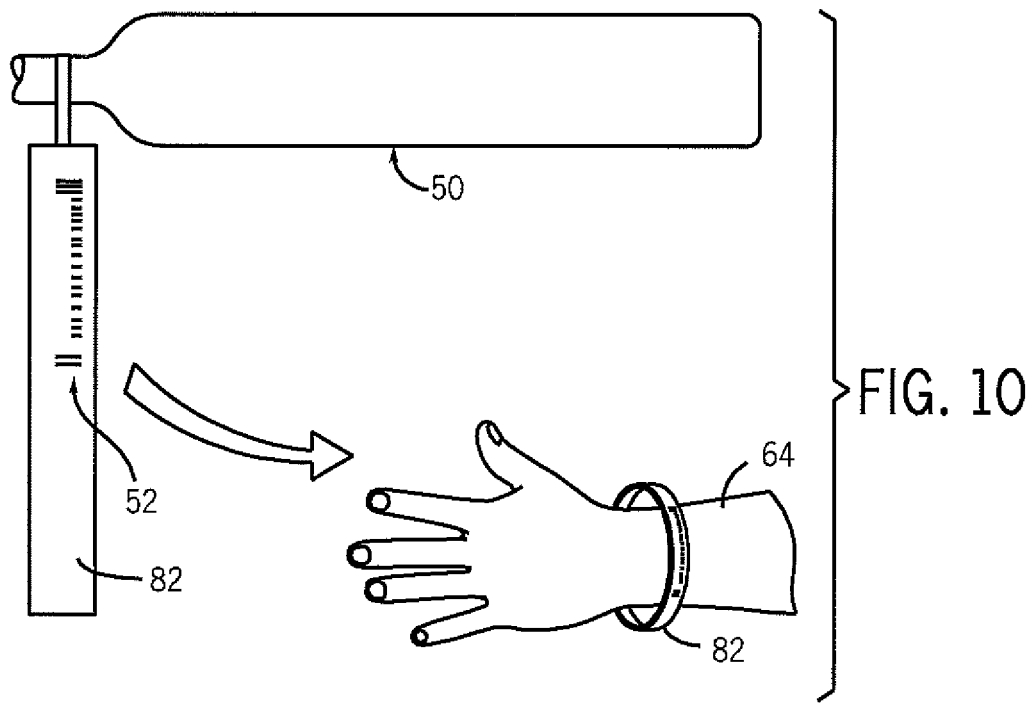
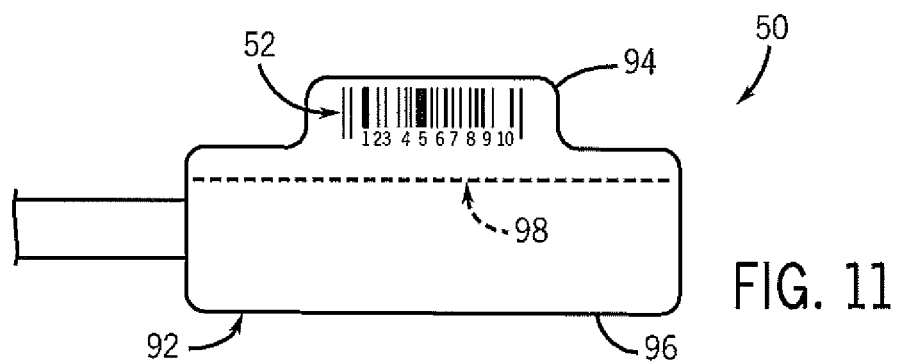
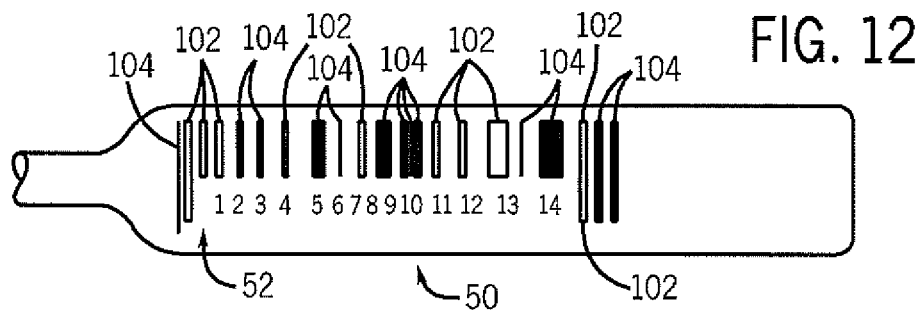
FIG. 10
FIG. 11
FIG. 12

SYSTEM AND METHOD FOR PROVIDING SENSOR QUALITY ASSURANCE

CROSS-REFERENCE TO RELATED APPLICATIONS

The present disclosure is related to co-pending U.S. patent application Ser. No. 12/494,997, entitled "System and Method for Linking Patient Data to a Patient and Providing Sensor Quality Assurance," and to co-pending U.S. patent application Ser. No. 12/494,986, entitled "System and Method for Controlling One or Both of Sensor Functionality and Data Access Based on Biometrics Data," each of which is herein incorporated by reference in its entirety for all purposes. Both co-pending applications are concurrently filed with and include the same inventors as the present application.

BACKGROUND OF THE INVENTION

The present disclosure relates generally to physiological monitoring instruments and, in particular, to a sensor that includes a mechanism for providing physiologic data and identification data, such as blood oxygen saturation data and a unique serial number, to a monitor, such as a pulse oximeter.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

There are numerous techniques and systems for monitoring a patient's physiology. For example, pulse oximetry may be used to continuously monitor physiologic characteristics of a patient. Pulse oximetry may generally be defined as a non-invasive technique that facilitates monitoring of a patient's blood characteristics. For example, pulse oximetry may be used to measure blood oxygen saturation of hemoglobin in a patient's arterial blood and/or the patient's heart rate. Specifically, in pulse oximetry, blood characteristic measurements may be acquired using a non-invasive sensor that passes light through a portion of a patient's blood perfused tissue and that photoelectrically senses the absorption and scattering of light through the blood perfused tissue. Various wavelengths of light may be used that may or may not pass through certain blood constituents. Indeed, a typical pulse oximetry sensor includes at least two light emitters that emit different wavelengths of light, and a light detector. Based on how much light at certain wavelengths is emitted and detected, and based on absorption and scattering characteristics of certain blood constituents, an estimate of the blood content may be made based on the detection results. For example, a typical signal resulting from the sensed light may be referred to as a plethysmographic waveform, which is a measurement of the absorbed and scattered light at different wavelengths. Once acquired, the plethysmographic waveform may be used with various algorithms to estimate an amount of blood constituent in the tissue, as well as other physiologic characteristics.

Some conventional sensors, such as conventional pulse oximetry sensors, may include an information element that stores information that can be read by a monitoring device to facilitate proper use of the sensor. For example, a pulse oximeter sensor may include a memory or a resistor that can be read by an oximeter. The information stored on the information element may include parameters about the sensor. For example, with regard to a pulse oximeter sensor, the information may indicate sensor type (e.g., neonatal, pediatric, or adult), the wavelengths of light produced by the emitters, and so forth. Certain data stored in the pulse oximeter sensor, such as the wavelengths of light associated with the emitters of the sensor, may be important for proper blood characteristic measurement. This information may be utilized in algorithms for determining values for one or more measured blood characteristics. Further, the information element may be utilized for security and quality control purposes. For example, the information element may ensure proper operation by preventing the sensor from functioning with improperly configured or unauthorized devices.

Due to the function of the information element, it is often necessary for sensor operation. Accordingly, the information element is often included in unapproved remanufactured sensors to enable their operation. However, such unauthorized remanufactured sensors may be unreliable and fail to function properly. Indeed, improper remanufacturing of a sensor or tampering with the sensor can impact the quality and reliability of the sensor, especially when such sensors include an information element with pertinent operational data stored thereon. For example, improper remanufacturing of a sensor may result in consistently incorrect measurements and/or cause malfunctions by coupling incompatible sensor components together. In a specific example, an information element for a neonatal oximeter sensor may be improperly incorporated into the body of an adult oximeter sensor during remanufacture. Thus, the information element incorporated into the remanufactured sensor may include settings for a neonatal application that do not correspond to the wavelengths associated with the light emitters of the remanufactured sensor, which correspond to an adult application. Such remanufacturing can cause improper operation and incorrect measurement of physiological characteristics.

BRIEF DESCRIPTION OF THE DRAWINGS

Advantages of present embodiments may become apparent upon reading the following detailed description and upon reference to the drawings in which:

FIG. 1 is a perspective view of a patient physiological data measurement system in accordance with an exemplary embodiment of the present disclosure;

FIG. 2 illustrates a sensor including an optical machine-readable representation of data in accordance with an exemplary embodiment of the present disclosure;

FIG. 7 illustrates a sensor including a loosely attached layer with an optical machine-readable representation of data printed thereon in accordance with an exemplary embodiment of the present disclosure;

FIG. 8 illustrates a sensor including an expansive bandage layer positioned over a sensor body, wherein the bandage layer includes an optical machine-readable representation of data printed thereon in accordance with an exemplary embodiment of the present disclosure;

FIG. 9 illustrates a sensor and a separate band attached to a clear plastic layer to facilitate attachment of the sensor and the band to a patient such that the sensor and band are separate, wherein the band includes an optical machine-readable representation of data printed thereon in accordance with an exemplary embodiment of the present disclosure;

FIG. 10 illustrates a sensor and an armband attached together and then detached with the armband attached to a patient, wherein the armband includes an optical machine-readable representation of data printed thereon in accordance with an exemplary embodiment of the present disclosure;

FIG. 11 illustrates a sensor with an optical machine-readable representation of data printed on a detachable portion of a sensor bandage in accordance with an exemplary embodiment of the present disclosure; and FIG. 12 illustrates a sensor with a bandage including an optical machine-readable representation of data printed in two different types of ink in accordance with an exemplary embodiment of the present disclosure.

DETAILED DESCRIPTION OF SPECIFIC EMBODIMENTS

Figure 3:
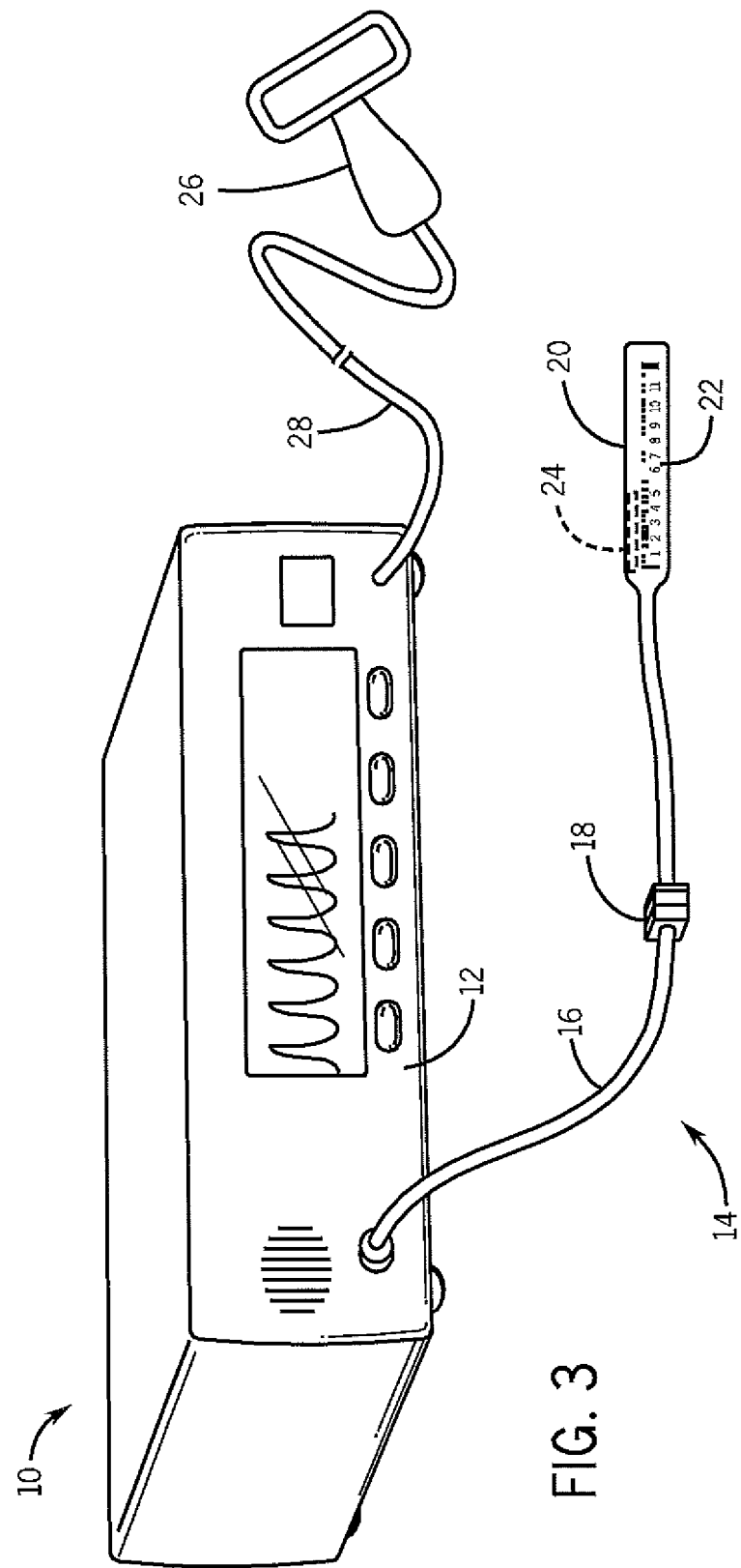
FIG. 3 is a perspective view of a patient physiological data measurement system including an attached optical reader in accordance with an exemplary embodiment of the present disclosure.

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Embodiments of the present disclosure relate, in general, to a sensor for measuring patient physiological characteristics. For example, present embodiments may include a pulse oximeter sensor that functions to measure oxygen content in a patient's blood. More particularly, present embodiments are directed to sensor designs and corresponding hardware to prevent remanufacture of the sensor or make such remanufacture impractical. Indeed, it is now recognized that unauthorized remanufacture of a sensor can create issues with proper operation of the sensor, and, thus, it is desirable to prevent such practices. Accordingly, present embodiments are directed to improving sensor quality assurance by preventing sensor remanufacture.

Specifically, embodiments of the present disclosure relate to a sensor that includes a functional component and an optical machine-readable representation of data (OMRD), wherein the functional component and the OMRD cooperate to substantially prevent remanufacturing of the sensor. In other words, present embodiments include a functional component (e.g., a memory) and an OMRD (e.g., barcode) that cooperate to prevent efficient remanufacture of the sensor. For example, in one embodiment, a pulse oximeter sensor includes a sensor memory that prevents the sensor from functioning unless a particular barcode is scanned by a monitor. The barcode may be printed on the sensor packaging. Further, the barcode may be destroyed after a single use of the sensor due to the location of the barcode, the material used to print the barcode, and so forth. For example, the barcode may be printed on a portion of the sensor that couples with the patient and tears away from the sensor when removed. Thus, remanufacturing the sensor may be exceedingly difficult because the sensor will not work without receiving the barcode data, which is generally unique to the sensor, and the barcode data is encoded in a printed barcode that is typically destroyed after a single use of the sensor.

In other exemplary embodiments, a sensor may include various types of OMRD, such as barcode, machine-readable patterns, machine-readable text, and so forth. Further, the OMRD may be printed in ink that fades or that is not visible to the human eye, printed on components of the sensor that break away when removed, or otherwise printed in such a manner as to make later access to the OMRD difficult or impossible. Thus, remanufacture of the sensor may be substantially prevented. For example, as indicated above, the sensor may include an information element disposed therein to facilitate measurement and ensure quality control. This information element may be configured to prevent the sensor from functioning unless the data from a specifically assigned OMRD is received by the information element. Because the OMRD may be specific to the information element, remanufacture of the sensor becomes difficult. Indeed, in order to remanufacture the sensor, the OMRD would have to be reproduced, which may be economically inefficient for potential remanufacturing entities. Furthermore, a potential remanufacture of the sensor may include added difficulty because the OMRD may be substantially destroyed or separated from functional components of the sensor after a single use of the sensor.

FIG. 1 is a perspective view of a patient physiological data measurement system in accordance with an exemplary embodiment of the present disclosure. Specifically, FIG. 1 includes a pulse oximeter system, which is generally indicated by reference numeral 10. The system 10 includes a specially programmed computer or monitor 12 (e.g., a pulse oximeter) that communicatively couples via a cable or wirelessly to a sensor 14. The sensor 14 includes a sensor cable 16, a connector plug 18, and a body 20 configured to attach to a patient. In the illustrated embodiment, the body 20 of the sensor 14 is generally planar and configured for application to a patient's skin.

In accordance with present embodiments, the body 20 of the sensor 14 may be configured to couple with a patient's earlobe, finger, foot, forehead, or other locations on the patient that facilitate non-invasive measurement of desired physiological data (e.g., pulse rate and/or blood oxygen saturation). In another embodiment, the sensor 14 may be configured for invasive operation and the body 20 may be configured for insertion into a patient. The sensor cable 16 and connector plug 18 may enable electronic communication from the sensor 14 to the monitor 12, and facilitate coupling and/or decoupling the sensor 14 from the monitor 12. In some embodiments, the sensor 14 may couple directly to the monitor 12 via the sensor cable 16. In other embodiments, the sensor 14 may communicate with the monitor 12 wirelessly (e.g., via radio waves) and may not include the cable 16 or the connector plug 18.

An OMRD 22 may be included on or with the sensor 14. In some embodiments, the OMRD 22 may include barcode, as illustrated in FIG. 1. In other embodiments, the OMRD 22 may include machine-readable graphic features and/or text, as illustrated by the sensor 14 depicted in FIG. 2. Indeed, the OMRD 22 may include or be incorporated into a trademarked symbol or word such that potential remanufacturing entities could not reproduced the OMRD 22 without violating trademark laws. The OMRD 22 may be printed, etched, included on a label that is attached via adhesive, and so forth. In the embodiment illustrated by FIG. 1, the OMRD 22 is positioned on a portion (e.g., an outer bandage portion) of the sensor 14 that is accessible when the sensor is attached to a patient. As will be discussed in further detail below, the OMRD 22 may be utilized in conjunction with an information element 24 of the sensor 14 to provide quality assurance and prevent unauthorized remanufacture of the sensor 14 in accordance with present embodiments. In the embodiment illustrated by FIG. 1, the information element 24 is disposed within the sensor body 20. However, in other embodiments, the information element 20 may be attached to an outer portion of the sensor body 20, disposed within the sensor cable 16, disposed within the connector plug 18, or included in some other fashion.

The OMRD 22 may be read with an optical reader 26, such as a barcode scanner. In some embodiments, the optical reader 26 may be integral with a main body of the monitor 12, as illustrated in FIG. 1. In such embodiments, to scan the OMRD 22, the portion of the sensor 14 including the OMRD 22 may be passed in front of the optical reader 26. Thus, the optical reader 26 may read and convert the OMRD 22 into data that can be communicated to a memory of the monitor 12 and so forth. However, in some embodiments, as illustrated in FIG. 3, the optical reader 24 (e.g., a scanning gun) may be coupled to the monitor 12 via a reader cable 28. The reader cable 26 may be sufficiently long to facilitate scanning the OMRD 22 in various locations relative to the monitor 12. For example, the sensor 14 may be coupled to a patient, and the OMRD 22 may be printed on an outer portion of the sensor body 20 such that it is accessible. Thus, it may be desirable for the reader cable 28 to be long enough to facilitate movement of the optical reader 26 over the sensor 14 instead of having to move the sensor 14, and, thus, the patient, to the optical reader 26. In fact, in some embodiments, the optical reader 26 may wirelessly communicate with the monitor 12 to facilitate reading the OMRD 22 on the sensor 14 without moving the sensor 14 to the monitor 12. Additionally, while the embodiment illustrated in FIG. 3 shows the optical reader 26 coupled directly to the monitor 12, in other embodiments, the optical reader 26 may be coupled to the monitor 12 via the sensor cable 16. Furthermore, in some embodiments, the optical reader 26 may not communicate with the monitor 12, but, rather, the optical reader 26 may communicate directly with the sensor 14 or the information element 24.

Figure 4:
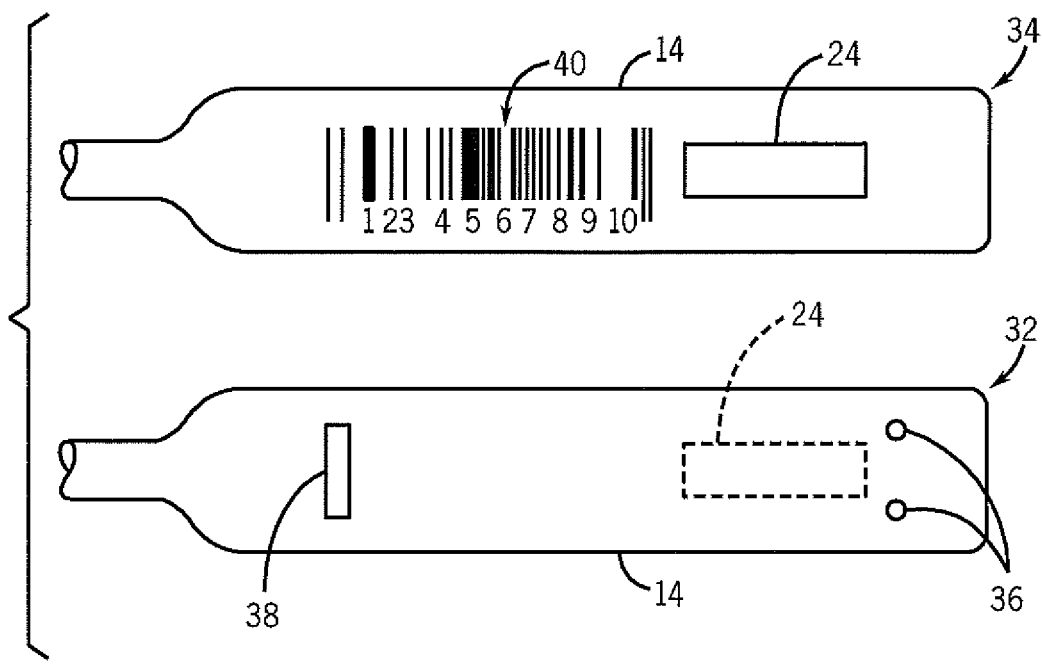
FIG. 4 illustrates a front view and a back view of a sensor including an optical machine-readable representation of data printed on the back in accordance with an exemplary embodiment of the present disclosure.

FIG. 4 illustrates a front portion 32 and a back portion 34 of the sensor 14 in accordance with present embodiments. Specifically, in the illustrated embodiment, the sensor 14 is a pulse oximeter sensor that includes a pair of emitters 36 (e.g., a red emitter and an infrared emitter) configured to emit light waves, and a photodiode detector 38 that is arranged to detect the emitted light waves. Such sensors are typically configured to attach to a patient's finger, foot, forehead, or earlobe to facilitate measurement of blood characteristics in the associated tissue. For example, the sensor 14 may be adapted to project light from the emitters 36 through the outer tissue of a finger and into the blood vessels and capillaries inside, and detect the emitted light at the detector 38 as the light emerges from the outer tissue of the finger. In operation, the detector 38 may generate a signal based on the detected light and provide the signal to the monitor 12, which may determine blood oxygen saturation based on the signal. For example, the monitor 12 may utilize the signal to display a plethysmographic waveform.

Figure 5:
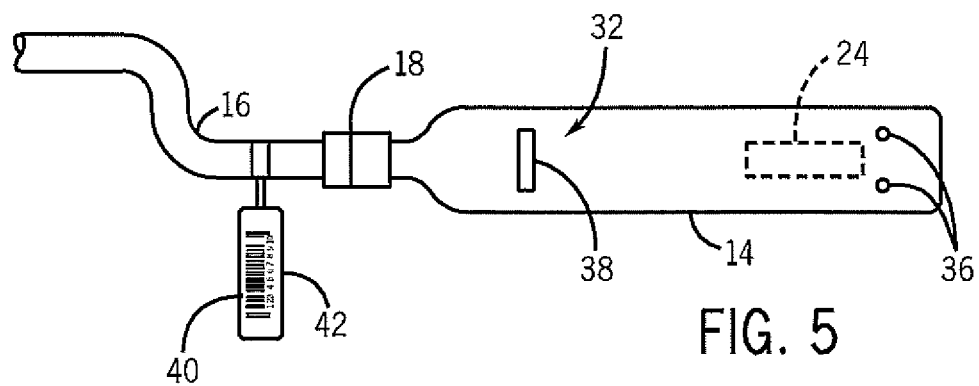
FIG. 5 illustrates a sensor with an attached tag, wherein the tag includes an optical machine-readable representation of data printed thereon in accordance with an exemplary embodiment of the present disclosure.
Figure 6:
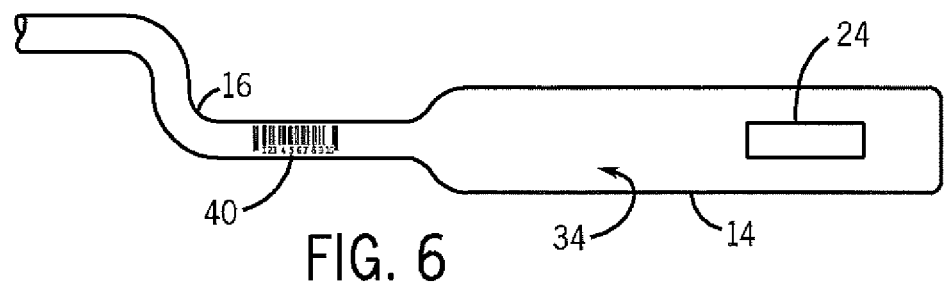
FIG. 6 illustrates a sensor with an optical machine-readable representation of data printed on a cable of the sensor in accordance with an exemplary embodiment of the present disclosure.

The front portion 32 of the sensor 14 is configured for placement adjacent a patient. Thus, the back portion 34 of the sensor 14 faces away from the patient when the sensor 14 is properly attached. Accordingly, the back portion 34 remains accessible to the optical reader 26 during use and includes an OMRD in accordance with present embodiments. Specifically, in the illustrated embodiment, the sensor 14 includes a barcode 40 printed on the back portion 34. In other embodiments, the barcode 40 or some other OMRD may be positioned on some other portion of the sensor or even separate from the sensor. For example, the barcode 40 may be printed on a tag 42 attached to the sensor 14 or attached to the sensor cable 16, as illustrated in FIG. 5. In another embodiment, as illustrated by FIG. 6, the barcode 40 may be printed directly on the sensor cable 16. In yet another embodiment, the barcode 40 may be printed on a separate item, such as a patient armband or the like. In some embodiments, the barcode 40 may be disposed on a sticker that is then attached to a portion of the sensor 14 or that is provided with the sensor 14 for attachment to the patient. Further, in some embodiments, the barcode may be engraved instead of printed. Engraving the barcode 40 or some other OMRD may facilitate the destruction of the barcode 40 after a single use because it will facilitate tearing upon removal of the sensor 14.

Further, as discussed above, the sensor 14 includes the information element 24, which may be internal or external to the sensor 14, and which stores data. For example, the information element 24 may store data that relates to disabling or enabling the functionality of the sensor 14. In one embodiment, the information element 24 may include a memory device (e.g., ROM) that stores data corresponding to data indicated by the OMRD 22 disposed on the sensor 14. A correlation between the data of the OMRD 22 and the data stored on the information element 24 may be required for the sensor 14 to function. For example, a processor in the monitor 12 or the sensor 14 may compare the data stored in the information element 24 with the data identified by scanning the OMRD 22 and determine whether the data matches. If the data does not match, the sensor 14 and/or the monitor 12 may prevent operation of the sensor 14 and/or provide an error indication (e.g., an alarm). In other embodiments, a combination of the data retrieved from the OMRD 22 and the data stored in the information element 24 may be required to enable functionality. For example, the OMRD 22 may include data that points to a storage location in the information element 24 for comparison.

Various techniques may be utilized to prevent copying and/or erasing the information element 24 for reuse. For example, to prevent copying of data from the information element 24, the data corresponding to the data represented by the OMRD 22 may be scattered in different memory locations. Thus, a correspondence between the data of the OMRD 22 and the data in the information element 24 may be difficult to discern. Further, encryption of the data may be employed. In one embodiment, an encryption feature, such as an encrypted signature, may be included on the information element 24. Accordingly, if the information element 24 is erased in an attempt to remanufacture the sensor 14, the encryption feature will also be erased, which will prevent further use of the sensor 14 by monitors that require such an encryption feature.

With regard to the data encoded by the OMRD 22, the OMRD 22 may encode data that can be used to identify the name or the type of a particular sensor. The OMRD 22 may also be used to store a unique serial number for a particular sensor or a unique code which is assigned to each customer. In another instance, the OMRD 22 may be used to store information directly required for sensor operation, such as a single piece of calibration data that the monitor 12 can read and use to interpret remaining encrypted data stored in the information element 24. The single piece of calibration data may employ the same encryption scheme as that used to store the remainder of the calibration data in the information element 24. In some embodiments, the OMRD 22 may contain information required to decrypt the information stored in the information element 24. Further, the encryption scheme may vary from one sensor to another. This would require a potential remanufacturing entity to obtain and print a unique OMRD 22 for each sensor that is remanufactured.

Accordingly, in order for the sensor 14 and/or the monitor 12 to function, the data stored in the information element 24 must cooperate with or correspond to the data translated from the OMRD 22 by scanning the OMRD 22 with the optical reader 26. As a specific example, the information element 24 may include a memory that stores an encrypted string of numbers that should correspond to the numbers represented by the barcode 40 printed on a bandage portion of the sensor 14. Thus, when the barcode 40 is scanned by the optical reader 26, the encrypted data in the memory may be compared to the data obtained from the optical scan, and, if the data does not match, the sensor 14 and/or the monitor 12 may not function. This may prevent unauthorized remanufacture of the sensor 14 because it would be difficult to perform bulk remanufacturing operations. Indeed, each sensor would have to be specifically remanufactured to include the appropriate barcode. Further, the barcode 40 may be difficult to retrieve after use of the sensor 14.

It should be noted that, in some embodiments, the information element 24 may be manufactured with a blank portion for storing the data represented by the OMRD 22. Thus, the sensor 14 may essentially be generic relative to the OMRD 22 until the OMRD 22 is initially scanned and the associated data is communicated and stored in the information element 24. For example, in use, a unique OMRD 22, such as the barcode 40 included on the sensor 14 may be scanned by the optical reader 26. Upon scanning the barcode 40, the associated data may be stored in the memory 24 and the sensor 14 may be enabled to operate. In some embodiments, scanning any manner of data will not necessarily enable operation. Rather, it may be necessary for the data to have a certain format or include certain basic information. Thus, once the proper type of data has been scanned into the memory 24, the sensor 14 may be enabled to operate. However, subsequent operation (e.g., operation after the sensor 14 has been powered down or detached from the monitor 12) may be prevented unless an identical barcode value is scanned and communicated to the memory 24. Accordingly, the sensor 14 may be originally manufactured such that it can be electronically coupled with any barcode having the proper type of encoded data by storing that data on the sensor 14. However, reuse of the sensor 14 is prevented unless a barcode identical to that initially scanned into the memory 24 is reproduced and utilized to activate the sensor 14 for subsequent uses.

As a specific example of an operational procedure in accordance with present embodiments, when a sensor is connected to a monitor, the monitor may recognize the connection to the sensor and prompt a user to scan a barcode with an optical scanner. Further, a memory field in a memory device of the sensor may be read because the memory field is intended to store barcode data. If no barcode data is present in the memory field, data retrieved from the scanned barcode may be written to the memory field. Indeed, the data retrieved from the scanned barcode may be transmitted from the monitor or transmitted directly from the scanner to the sensor memory for storage in the memory field. When data is initially stored in the memory field, the sensor may begin to function, or a second scan of the barcode on the sensor may be required to confirm a correspondence between the data stored in the sensor and the data represented by the barcode. Alternatively, if data, such as a unique serial number, is present in the memory field when the sensor is initially connected, the stored data may be compared to the barcode data obtained from the barcode via the optical scanner. If the data stored in the sensor memory corresponds to that obtained from the barcode, the sensor may be allowed to operate. If it is different, the monitor may reject the sensor and/or indicate that the sensor is not an approved sensor.

In one embodiment, an OMRD associated with a sensor may store data that is required for sensor operation. For example, a barcode printed on a sensor bandage may include calibration data, data required to decrypt information provided by the sensor, data that combines with data stored in a sensor memory to enable cooperation with a monitor, and so forth. Thus, the appropriate OMRD (e.g., barcode) is required for proper sensor operation, and an error in printing a new OMRD would prevent further use of the sensor. Further, because an OMRD is uniquely associated with a specific sensor, simply replicating a single OMRD for multiple sensors would only enable the associated sensor to be reused. For example, if a barcode is scanned to reveal data that does not match or correspond to the data in a memory of a particular sensor, the sensor will not work because a processor of the associated monitor or of the sensor itself will compare the data and recognize differences and/or attempt to utilize the data in combination and fail.

Various techniques, sensor components, and packaging procedures may be utilized to further prevent remanufacture of sensors in accordance with present embodiments. Indeed, sensors may be manufactured or packaged such that there is a high likelihood that an OMRD provided with the sensor will be destroyed, become unreadable, or disassociated from functional features of the sensor (e.g., an information element) after a single use of the sensor. For example, as illustrated in FIG. 7, a sensor 50 may be provided with an OMRD 52 disposed on an outer layer 54 of the sensor 50. The outer layer 54 may be attached to a main body 56 of the sensor 50 with a very light adhesive, while the main body 56 includes a more substantial adhesive on a functional side 58 of the sensor 50 for attaching to a patient. Thus, the functional side 58 of the sensor 50 may be coupled to a patient, leaving the OMRD 52 exposed, and, when the sensor 50 is removed, the outer layer 54 will likely become dislodged from the sensor 50, as illustrated by the arrow 60 in FIG. 7. Further, the outer layer 54 may be made of material that will not hold up to sterilization procedures. For example, exposure of the outer layer 54 to certain types of radiation or materials used in sterilization may cause the outer layer 54 to dissolve or discolor such that the OMRD 52 becomes unreadable.

In another embodiment, as illustrated by FIG. 8A, the sensor 50 may be provided with an expansive bandage 62 that completely covers and expands beyond the perimeter of the main body 56 of the sensor 50 such that it facilitates attachment of the sensor 50 to a patient. The OMRD 52 may be printed on the bandage 62. Because the bandage 62 completely covers the main body 56, removal of the sensor 50 may be achieved by first removing the bandage 62 from a patient 64, as illustrated in FIG. 8B. Thus, after a single use, the OMRD 52 printed on the bandage 62 may be separated from the functional features of the sensor 50, which will limit the ability to reproduced the OMRD 52 on a remanufactured sensor. To encourage removal of the bandage 62 in a manner that separates it from the main body 56, a tab 66 may be provided to facilitate removal. For example, the tab 66 may be an extension of the bandage 62 that does not included adhesive, and, thus, is easy for a clinician to grab and pull away from the patient 64. Additionally, specific instructions for use may be provided that indicate a user should peel off the bandage 62 and discard it during removal to protect against contributing to the remanufacture of sensors that may malfunction. Further, the bandage 62 may be loosely attached to the main body 56, and or the main body 56 may include an adhesive for attaching to the patient 64 to encourage separation of the bandage 62 from the main body 56 during detachment of the sensor from the patient 64.

FIG. 9 illustrates yet another embodiment that may encourage separation of the OMRD 52 from the functional features of the sensor 50 after a first use of the sensor 50. Specifically, the sensor 50 and a separate label 72 may be lightly adhered to a base sheet 74, which is illustrated as a clear sheet of plastic, and both the sensor 50 and the label 72 may include adhesive material for attaching to a patient. For example, with regard to the embodiment illustrated by FIG. 9, the sensor 50 and the label 72 may be attached to a patient's forehead by exposing adhesive on the sensor 50 and the label 72 opposite the base sheet 74, pressing the sensor 50 and the label 72 against the patient's forehead through the base sheet 74, and then peeling the base sheet 74 away. Thus, the sensor 50 and the label 72, which includes the OMRD 52, are separately attached to the patient, and will likely be disassociated after a single use. A similar result may be obtained by providing the sensor 50 with an arm band 82 that is initially attached and that may be separated and attached to the patient 64, as illustrated in FIG. 10. The arm band 82 includes the OMRD 52. Because the arm band 82 may be removed and attached to the patient, the OMRD 52 will likely be discarded separate from the functional features of the sensor 50 after the first use of the sensor 50.

FIG. 11 illustrates another embodiment that facilitates disassociation of the OMRD 52 from functional components of the sensor 50 after a single use. Specifically, FIG. 11 includes the sensor 50 with a bandage component 92 for attachment of the sensor 50 to a patient, wherein the bandage component 92 includes a tear-away portion 94 that is separated from a main portion 96 of the bandage component 92 by perforations 98. The tear-away portion 94 includes the OMRD 52 printed thereon. Accordingly, when the sensor is removed 50, the perforations 98 will encourage tearing and separation of the OMRD 52 from the functional features of the sensor 50. In some embodiments, the perforations 98 may be positioned such that the OMRD 52 itself becomes mangled and unreadable. For example, the perforations 98 may combine to form a jagged line along the OMRD 52.

In some embodiments, the OMRD 52 may be printed on the sensor 50, on a sensor cable, or on a tag associated with the sensor 50 with a medium that reacts in some manner to exposure to air, sterilization, and so forth, or that makes access to information difficult. For example, applying the sensor 50 may expose the ink used to make the OMRD 52 to air or to the patient's skin, which may initiate a reaction that degrades the ink over time such that it can no longer be read. As another example, the OMRD 52 may be printed with an ink that is not substantially visible to the human eye or that reacts with a chemical or radiation typically used in sterilization techniques. For example, typical types of chemicals utilized in sterilization include alcohol, peroxide, and so forth. Examples of light waves utilized in sterilization may include gamma and/or electron-beam irradiation.

The ink or material utilized to form the OMRD 52 may include a chemical that essentially disappears, degrades, or becomes visible upon exposure to ethanol, steam, radiation, or the like. Specifically, as illustrated in FIG. 12, the OMRD 52 may include a barcode wherein certain bars are printed in an ink that is not initially visible, as represented by clear bars 102, while other bars are always visible, as represented by dark bars 104. When the clear bars 102 are exposed to sterilization chemicals and/or radiation, the clear bars 102 may become visible. In other embodiments, all or a portion of the bars 102, 104 may disappear when exposed in some manner to sterilization. Thus, such sterilization would prevent functionality as a remanufactured sensor because the OMRD 52 would be gone, unreadable, or include wrong information. In an embodiment wherein features are added to the OMRD 52 upon sterilization, such as adding visible bars to a barcode by making certain ink visible, a processing feature (e.g., a microprocessor in the sensor 50 or an oximeter) may be programmed to scramble all or some of the entries in an information element of the sensor when such extra bars are detected. In some embodiments, the clear bars 92 may represent bars printed in an ink that is not visible to the human eye but that is detectable by a scanner, which may cause confusion for potential remanufacturing entities.

Remanufacture of a sensor that was originally assembled in accordance with present embodiments may be achieved, but may be difficult. For example, a used sensor may be sterilized and reassembled to include the original or a copy of the OMRD associated with the sensor. Further, various components may be replaced and/or reused. In some embodiments, certain functional features, such as an information element, of the sensor may be included in a new or remanufactured sensor body and a copy of the OMRD may be provided on or with the remanufactured sensor. Reprocessing may include erasing all of the information on the information element (e.g., memory) of a sensor, which would also erase encrypted information required for operation. Once the information element is blank, new encryption information could be included with a blank OMRD code field (e.g., a field for storing data that should correspond to the data encoded by an OMRD associated with the sensor) by an entity with the proper encryption knowledge. In some embodiments, this may include wiping a memory and pointing to a new memory section for storing encryption data and/or OMRD code.

It should be noted that the information element may include any of various different types of memory in accordance with present embodiments. For example, write-once memory (WOM) and/or rewritable memory (EPROM, EEPROM) may be utilized. These different types of memory would have an impact on attempts to remanufacture a sensor. With regard to write-once memory, for example, the write-once memory would be invalidated by any attempt to erase the biometric data code field because it cannot be rewritten. With regard to rewritable memory or write-many memory, the biometric data code field could be erased and data could be written over it. However, such a memory may be prevented from functioning in accordance with present embodiments because of encryption of the biometric data field, scattering of the biometric data field, and/or a special field indicating that the biometric data has been written (e.g., a recorded date of rewriting).

While the embodiments set forth in the present disclosure may be susceptible to various modifications and alternative forms, specific embodiments have been shown by way of example in the drawings and have been described in detail herein. However, it should be understood that the disclosure is not intended to be limited to the particular forms disclosed. Indeed, the present techniques may not only be applied to measurements of blood oxygen saturation, but these techniques may also be utilized for the measurement and/or analysis of other physiological characteristics. The disclosure is to cover all modifications, equivalents, and alternatives falling within the spirit and scope of the disclosure as defined by the following appended claims.

What is claimed is:

1. A sensor, comprising:
   an optical machine-readable representation of data (OMRD) representing data related to the sensor, the OMRD being disposed on the sensor or packaged therewith; and
   an information element configured to store data, wherein operation of the sensor with a monitor is enabled upon determination of a correlation between data stored on the information element and the data represented by the OMRD.

2. The sensor of claim 1, wherein the OMRD is included on a body of the sensor.

3. The sensor of claim 1, wherein the OMRD is included on a tag attached to the sensor.

4. The sensor of claim 1, wherein the OMRD is included on a feature that is separate from the sensor but packaged with the sensor.

5. The sensor of claim 1, wherein the OMRD is printed with a material that is configured to degrade when exposed to air, sterilization chemicals, certain types of radiation utilized in sterilization, or a patient's skin.

6. The sensor of claim 1, wherein all or a portion of a material utilized to print the OMRD is configured to become visible when exposed to radiation or chemicals associated with sterilization.

7. The sensor of claim 1, wherein the OMRD encodes a sensor identification code that is also stored in the information element.

8. The sensor of claim 1, wherein the OMRD comprises a barcode or a trademark.

9. The sensor of claim 1, wherein the OMRD encodes information required for decryption of information stored in the information element.

10. A system for facilitating the monitoring of physiological data, comprising:
    an optical scanner configured to translate an optical machine-readable representation of data (OMRD) into electronic scanned data, the OMRD representing data related to the sensor; and
    a monitor comprising a memory device and a processor programmed to:
       receive the electronic scanned data from the optical reader;
       compare or combine the electronic scanned data with electronic stored data in a sensor that is configured to electronically communicate with the monitor;
       disable operation with the sensor if the scanned data does not match the stored data or if combination of the scanned data and the stored data provides insufficient information to enable operation of the sensor with the monitor; and
       enable operation of the sensor if the scanned data matches the stored data or if combination of the scanned data and the stored data provides sufficient information to enable operation of the sensor with the monitor.

11. The system of claim 10, wherein the monitor comprises a pulse oximeter.

12. The system of claim 10, comprising the sensor, wherein the sensor comprises the OMRD printed on a sensor body, a sensor cable, or a tag coupled to the sensor.

13. The system of claim 10, wherein the monitor is configured to store the scanned data in a memory field of the sensor as the stored data when no data is already present in the memory field.

14. The system of claim 10, wherein upon detecting coupling of the sensor with the monitor, the monitor is configured to require scanning of the OMRD prior to enabling the sensor to collect physiological data.

15. A method of remanufacturing a sensor, comprising:
    sterilizing a used sensor body including a used sensor memory or installing the used sensor memory into a new sensor body, wherein the used sensor memory includes a memory field storing data; and
    providing a copy of an optical machine-readable representation of the data (OMRD) on the new or used sensor body or on a component packaged with the new or used sensor body, the OMRD representing data related to the sensor, and wherein operation of the sensor with a monitor is enabled upon determination of a correlation between the data stored on the used sensor memory and the data represented by the OMRD.

16. The method of claim 15, comprising wiping all or a portion of the used sensor memory.

17. The method of claim 15, comprising writing over the memory field with new data or reconfiguring the used sensor memory to store new data obtained from a scan procedure to a different memory field.

18. The method of claim 16, comprising storing an encryption signature on the used sensor memory.

19. The method of claim 16, wherein providing the copy of the OMRD comprises recycling an original OMRD.

20. A sensor, comprising:
    an optical machine-readable representation of data (OMRD) representing data related to the sensor, the OMRD being disposed on the sensor; and
    an information element configured to store data corresponding to the OMRD, wherein the OMRD is configured to disappear when exposed to air.

21. A sensor, comprising:
    an optical machine-readable representation of data (OMRD) representing data related to the sensor, the OMRD being disposed on the sensor; and
    an information element configured to store data corresponding to the OMRD, wherein the OMRD is configured to become a different OMRD when exposed to gamma radiation, electron-beam radiation, alcohol, peroxide, ethanol, or combinations thereof, and wherein the information element is not configured to store data corresponding to the different OMRD.

22. The sensor of claim 20, wherein the OMRD is configured to disappear during a single use.

23. A sensor, comprising:
    an optical machine-readable representation of data (OMRD) representing data related to the sensor, the OMRD being disposed on the sensor; and
    an information element configured to store data corresponding to the OMRD, wherein the OMRD is configured to disappear when exposed to sterilization chemicals, gamma radiation, or electron beam-radiation utilized in sterilization.

24. The sensor of claim 1, wherein the OMRD encodes a sensor serial number.

25. The sensor of claim 1, wherein the OMRD encodes a customer code.

26. The sensor of claim 1, wherein the OMRD encodes calibration data for the sensor.

* * * * *